(12) United States Patent
Schlun et al.

(10) Patent No.: US 7,727,272 B2
(45) Date of Patent: Jun. 1, 2010

(54) BEARING STRUCTURE (75) Inventors: Martin Schlun, Herxheim (DE); Heiner Martin, Rostock (DE); Klaus-Peter Schmitz, Warnemuende (DE)

(73) Assignee: Biotronik GmbH & Co. KG (DE)

( * ) Notice: Subject to any disclaimer, the term of this patent is extended or adjusted under 35 U.S.C. 154(b) by 790 days.

(21) Appl. No.: 10/535,081

(22) PCT Filed: Nov. 12, 2003

(86) PCT No.: PCT/EP03/12643

§ 371 (c)(1),
(2), (4) Date: Dec. 21, 2005

(87) PCT Pub. No.: WO2004/043295

PCT Pub. Date: May 27, 2004

(65) Prior Publication Data

US 2006/0149352 A1    Jul. 6, 2006

(30) Foreign Application Priority Data

Nov. 13, 2002   (DE)   ................................ 102 53 633

(51) Int. Cl.
*A61F 2/06* (2006.01)
(52) U.S. Cl. ..................... 623/1.15; 623/1.16
(58) Field of Classification Search ................ 623/1.1, 623/1.15, 1.16, 1.5–1.54, 1.38
See application file for complete search history.

(56) References Cited

U.S. PATENT DOCUMENTS

| | | | | |
|---|---|---|---|---|
| 5,496,365 A | * | 3/1996 | Sgro | 623/1.2 |
| 5,776,181 A | * | 7/1998 | Lee et al. | 623/1.15 |
| 5,922,020 A | * | 7/1999 | Klein et al. | 623/1.15 |
| 6,013,091 A | | 1/2000 | Ley et al. | |
| 6,042,606 A | * | 3/2000 | Frantzen | 623/1.18 |
| 6,254,632 B1 | * | 7/2001 | Wu et al. | 623/1.15 |
| 6,423,090 B1 | * | 7/2002 | Hancock | 623/1.15 |
| 6,471,720 B1 | | 10/2002 | Ehr et al. | |
| 6,562,065 B1 | * | 5/2003 | Shanley | 623/1.15 |
| 6,626,935 B1 | * | 9/2003 | Ainsworth et al. | 623/1.15 |
| 6,805,705 B2 | * | 10/2004 | Hong et al. | 623/1.15 |
| 2002/0072792 A1 | | 6/2002 | Burgermeister et al. | |

(Continued)

FOREIGN PATENT DOCUMENTS

DE    19539449 A1    4/1997

(Continued)

*Primary Examiner*—Anhtuan T Nguyen
*Assistant Examiner*—Jocelin C Tanner
(74) *Attorney, Agent, or Firm*—Hahn Loeser & Parks, LLP; John J. Cunniff (57) ABSTRACT

A one-piece expandable flat bearing structure formed by at least partially elastically deformable struts which are separated from each other by openings in the bearing structure. The bearing structure can assume at least one compressed condition and at least one expanded condition and has at least one expansion direction. The bearing structure has anchor regions, from which spring struts, which are elastically resilient with respect to the anchor regions, extend to a resiliently deflectable end of the spring struts, a hinge strut adjoining said end. The spring struts and the hinge struts are of such a configuration and arrangement that both the compressed condition of the bearing structure and also the expanded condition of the bearing structure is stabilized by a spring action emanating from the spring struts.

15 Claims, 13 Drawing Sheets

U.S. PATENT DOCUMENTS

| | | |
|---|---|---|
| 2002/0072797 A1 | 6/2002 | Hays et al. |
| 2002/0107563 A1 | 8/2002 | Shanley |

FOREIGN PATENT DOCUMENTS

| | | |
|---|---|---|
| DE | 19731021 | 1/1999 |
| WO | WO 97/26840 | 7/1997 |
| WO | WO 99/44543 | 9/1999 |
| WO | WO 00/49971 | 8/2000 |

* cited by examiner

3 D-Model

FIG. 1B

2D-Development

FIG. 6B
3D-Model

FIG. 6A
2D-Development

3D-Model

FIG. 11B

2D-Development

BEARING STRUCTURE

BACKGROUND OF THE INVENTION

The invention concerns a one-piece expandable flat bearing structure. That bearing structure is formed by at least partially elastically deformable struts which are separated from each other by openings in the bearing structure. The bearing structure can assume at least one compressed condition and at least one expanded condition and has at least one expansion direction into which the bearing structure can expand from the compressed condition to the expanded condition.

The invention concerns in particular endoluminal prostheses and in particular stents with such a bearing structure.

The term flat bearing structure is here also used to denote such a bearing structure which forms, for example, the peripheral wall of a tubular article which is open at its two ends. Such a tubular article which is open at both ends is represented by per se known stents.

Stents are used in many cases as implantable vessel supports. Known stents are urethra stents as well as coronary stents and peripheral stents. Coronary stents serve to deal with vessel constrictions in the coronary blood vessels, so-called stenoses, by means of a radial supporting action which emanates from the stent. The same is implemented by peripheral stents for peripheral blood vessels.

Many stents of that kind are produced from a one-piece tube as the starting material by cutting, for example, by means of a laser. The cuts into the tube serving as the starting material provide a bearing structure of struts and openings which are disposed therein, which structure can be radially expanded in the case of stents. In particular, the expanded bearing structure is grid-like and has struts which enclose radial openings of greater or lesser size in the stent. Balloon-expandable stents and self-expandable stents are known. Self-expandable stents comprise for example a memory metal such as nitinol which, upon reaching a jump temperature, jumps from a first shape corresponding to the compressed condition of the stent, to a second shape corresponding to the expanded condition of the stent.

The balloon-expandable stents, which are of particular interest in the present context, do not automatically change from the compressed to the expanded-condition but rather are expanded by means of a balloon which is pumped up with a fluid in the interior of the stents. A balloon of that kind is generally arranged at the end of a balloon catheter which serves at the same time, for introducing the stent as far as the location to be treated at the vessel constriction. For that purpose, the stent is crimped onto the balloon. The stent is expanded by means of the balloon at the treatment location.

The demands made on stents of that kind are many and various. In order on the one hand to be well introduced into a blood vessel and on the other hand to sufficiently expand a stenosis, the bearing structure of the stent must be capable of being expanded from a compressed diameter, which is as small as possible, to a sufficiently large expanded diameter. The expanded bearing structure must also enjoy a sufficient radially acting bearing force, also referred to as radial strength, in order to reliably hold the vessel open. Further desirable properties are suitable surface coverage by the expanded stent, as well as appropriate behavior upon flexing about the longitudinal axis of the stent, as is frequently required in relation to blood vessels in the human body. A further demand on bearing structures for stents is that a balloon-expandable stent is to spring back again as little as possible after expansion by the balloon. More specifically, the consequence of such spring-back effect on the part of the bearing structure after expansion by a certain amount is that the bearing structure has to be expanded by that amount beyond the desired final dimension so that ultimately the bearing structure assumes the desired final stent dimension. That spring-back effect on the part of the bearing structure immediately after expansion when the balloon serving for expansion is deflated again, is referred to as recoil.

The co-operation of material property and stent design lead to the structural properties of the stent. To assess a stent design and for comparison with other stents, reference is made to characteristic values which are set forth in the following section. In order to obviate misunderstandings, it should be noted at this juncture that this involves pure engineering characteristic values for describing the stent properties, which are not to be confused with the situation in the vessel.

Recoil:

Recoil describes the elastic spring-back effect during or after evacuation of the balloon catheter. It is defined as the relative difference between the diameter at maximum pressure and the diameter after balloon evacuation.

Radial strength:

Radial strength specifies the maximum external pressure that the stent withstands. The characteristic value is the collapse pressure which is defined as the pressure at which the stent has collapsed.

Shortening:

The stent can shorten during stent dilation. The parameter describing that phenomenon is called shortening and is defined as the relative difference between the length prior to dilation and the final length.

Flexural stiffness:

The coronary vessels generally do not extend in a straight line but are twisted so that the stent should be as flexurally soft as possible for easy passage to the implantation location. In addition, flexurally soft stent designs permit stent implantation in curved and branched coronary vessels [4]. The flexural stiffness of stents is ascertained as structural stiffness E1 with the unit [Nmm] from a flexural test [5].

Further parameters:

The expansion behavior, crimpability and compliance are further considered.

Expansion behavior is determined by the balloon pressure at which the stent opens, free deployment of the struts takes place and so forth. Crimpability influences handling of the stent from the point of view of the cardiologist or machine crimping in the case of the complete systems.

It is very difficult to arrive at a relationship between the mechanical characteristic values of a stent and its biocompatibility and specifically hemocompatibility. Biocompatibility is composed of surface compatibility and structural compatibility. In the case of a stent, surface compatibility involves blood contact on the one hand and tissue contact with the vessel wall on the other hand. Structural compatibility extends from the mechanical supporting effect by way of flexural stiffness and the strut shape to the fluidic influences on the blood flow. The stent should not destroy the vessel, it should not result either in mechanical or toxic irritations and it should be athrombogenic in terms of blood contact.

The person skilled in the art is aware of a large number of bearing structures for stents, which all afford various advantages and conversely frequently also entail certain disadvantages. The known bearing structures, for example, can frequently be embodied only insufficiently or not at all with the materials which have a low modulus of elasticity. Most of the known bearing structures presuppose materials which can be well plastically deformed. That is important, in particular, in regard to the above-indicated requirement for keeping recoil as low as possible.

SUMMARY OF THE INVENTION

With that background in mind, an aspect of the present invention is to provide a bearing structure which satisfy the manifold demands on a bearing structure for a stent and which can also be implemented with materials of a low modulus of elasticity.

In accordance with the invention, that aspect is achieved by a bearing structure of the kind set forth in the opening part of this specification, which has anchor regions, from which spring struts which elastically return with respect to the anchor regions extend, to a resiliently deflectable end of the spring struts. A hinge strut adjoins the resiliently deflectable end of the spring struts. The spring struts and the hinge struts are of such a configuration and arrangement that the spring struts are firstly resiliently deflected transversely with respect to the expansion direction during the transition from the compressed condition to the expanded condition of the bearing structure by the folding-over hinge struts and finally recoil. At the same, time a respective central axis of the hinge struts is pivoted away about a hinge axis extending transversely with respect to the bearing structure beyond a reference axis which extends within the bearing structure transversely with respect to the expansion direction and transversely with respect to the hinge axis. The configuration and arrangement of spring struts and hinge struts is such that both the compressed condition of the bearing structure and also the expanded condition is stabilized by a spring action emanating from the spring struts.

The invention is based on the idea that materials of a low modulus of elasticity resiliently yield more easily to deformation forces, instead of plastically deforming. In that respect, elastic deformation of the bearing structure usually results in unwanted recoil.

Unlike all known bearing structures, the bearing structure which is described herein makes it possible to use the spring forces linked to the elastic deformation of the bearing structure for stabilization of the bearing structure both in the compressed condition and also and in particular in the expanded condition. The bearing structure described herein snaps virtually upon expansion into the expanded condition. The supporting effect of the bearing structure is not impaired somewhat by the spring forces but on the contrary is even further enhanced.

Hinge struts and spring struts in this bearing structure are of such a configuration and arrangement relative to each other that, by virtue of the spring action emanating from the spring struts, the spring struts apply to the hinge struts a moment which rotates the hinge struts after expansion of the bearing structure beyond a certain amount in the direction corresponding to the position of the hinge struts in the expanded condition.

Preferably, the two longitudinal ends of a respective hinge strut are respectively engaged by a spring strut which jointly rotate the hinge strut in the same direction about the hinge axis, that is to say, they apply a moment in the same direction to the hinge strut. For that purpose the two spring struts adjoining a respective hinge strut are preferably shaped and arranged in point-symmetrical relationship with each other.

The bearing structure involved here is basically suitable for many different uses. A particularly preferred use is one in which the bearing structure forms a peripheral wall of a stent.

The subject of the present application is thus also a stent with a bearing structure as described here.

In this respect, the bearing structure of the stent may be so arranged that the expansion direction extends in the peripheral direction of the stent so that the reference axis beyond which the hinge struts are pivoted extends in parallel relationship with or at a shallow angle to the longitudinal direction of the stent, while the hinge axis about which the hinge struts are hinged is oriented approximately radially with respect to the stent. Such an arrangement of the bearing structure imparts a high level of radial strength in the expanded condition even to a stent comprising a material with a low modulus of elasticity.

A bearing structure of that kind can be formed in particular also from plastic material or a magnesium alloy. By virtue of their low modulus of elasticity, those materials usually entailed major disadvantages when used as a material for stents. The subject-matter of this application is thus also stents which are of a bearing structure as described here and whose material is plastic material, in particular polymers or a magnesium alloy.

A particularly preferred stent is a stent comprising biodegradable material, in particular a magnesium alloy or a polymer such as poly-β-hydroxybutyric acid (PHB), poly-E-caprolacton (PCL) and poly-L-lactide (PLLA). A suitable polymer blend comprises 80% PLLA, 10% PCL and 10% triethylcitrate (TEC).

The above-described bearing structure may have openings which are cut so that the struts are separated from each other by cuts. Such cuts can be produced, for example, by means of a laser. In that case, a suitable starting material for a bearing structure for a stent is a tube portion comprising the stent material, which is subjected to further processing by laser cutting to afford the bearing structure.

The shape of the hinge struts which are separated by the cuts from the adjacent bearing structure, in particular from the spring struts, may be S-shaped or W-shaped in the compressed condition of the bearing structure.

The cuts may have end regions which are enlarged to avoid a notch effect and in particular to reduce edge fiber stretching in the end region of the cuts. Alternative solutions for reducing edge fiber stretching in the end region of the cuts may be set forth in the context of the specific description hereinafter and illustrated in the drawing.

The spring struts may be so shaped that, in the proximity of the anchor regions, they involve a larger cross-sectional area than in the region of their resiliently deflectable ends. In particular, it has proven to be advantageous if the spring struts steadily narrow starting from the anchor regions towards the resiliently deflectable ends. The hinge struts on the other hand are of a substantially uniform cross-section in transverse relationship with their central axis. It may be particularly preferred if a transitional region of a cross-section which is reduced with respect to the hinge strut is provided between a respective resiliently deflectable end of a spring strut and the hinge strut adjoining same.

BRIEF SUMMARY OF THE SEVERAL VIEWS OF THE DRAWINGS

The invention will now be described in greater detail by means of embodiments, by way of example with reference to the accompanying drawings in which:

FIG. 12 shows a 3D-model of the first variant for a urethra stent with a development as shown in FIG. 11a, FIG. 12a shows the development of a bearing structure for a second variant of a urethra stent.

DETAILED DESCRIPTION OF THE INVENTION

Figure 1A:
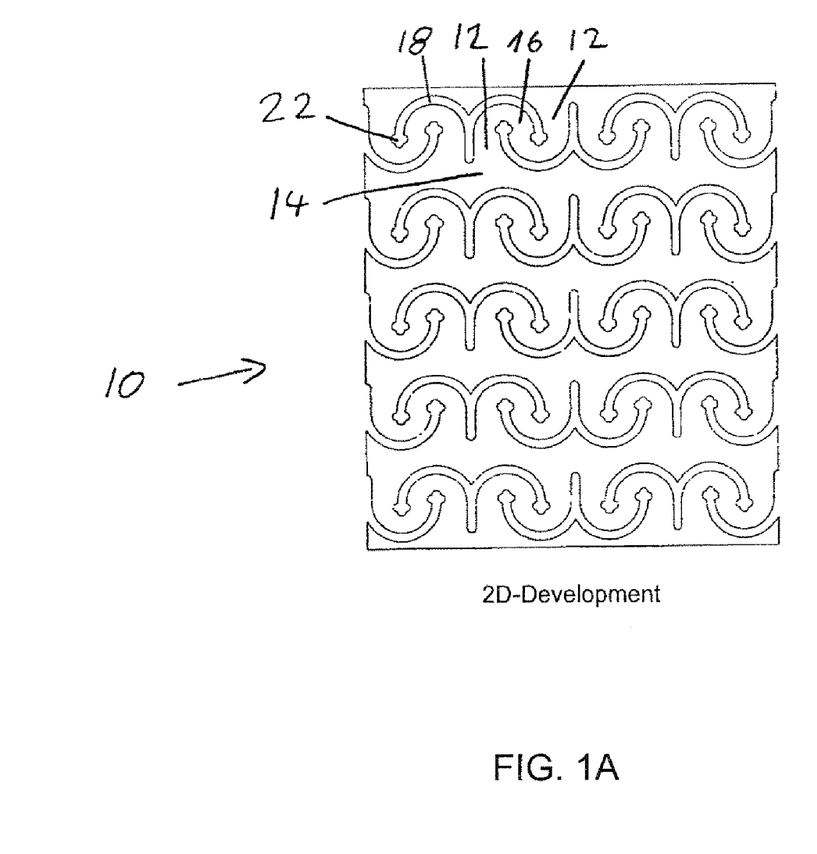
FIG. 1a shows a development of the peripheral wall of a first variant of a coronary stent.

The development of a bearing structure 10 for a first variant of a coronary stent has spring struts 12 which respectively start from an anchor region 14 and enclose in pairs between them a respective hinge strut 16.

Figure 1B:
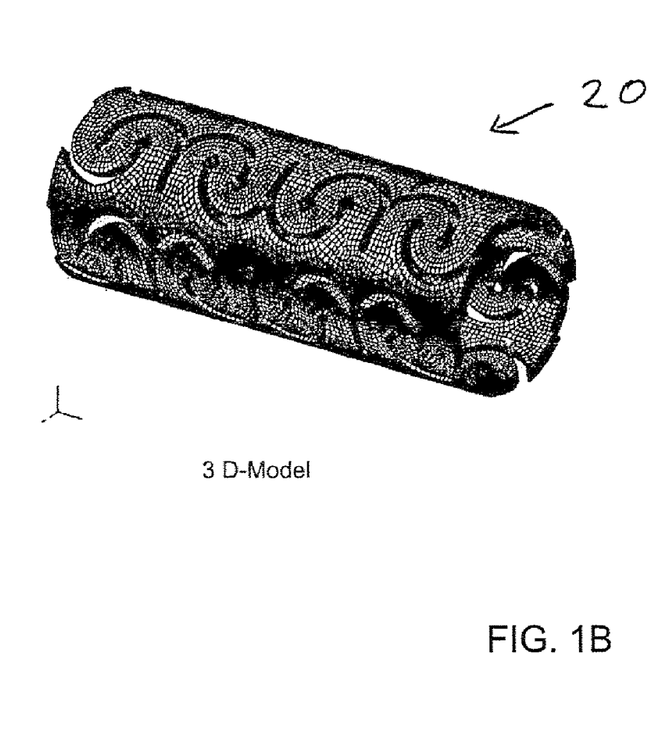
FIG. 1b shows a three-dimensional model of a portion of the first variant of a coronary stent with a bearing structure corresponding to the development in FIG. 1a, FIG. 2 shows three views which serve to explain the mode of operation of the bearing structure and which from left to right correspond to a compressed condition, a transitional condition and an expanded condition.

The development in FIG. 1a corresponds to a coronary stent, of which a longitudinal portion 20 is shown in FIG. 1b in the form of a 3D-model. Spring struts 12 and hinge struts 16 are separated from each other by cuts 18 forming openings. The cuts 18 are all of a W-shape in the embodiment of FIG. 1a.

All coronary stents illustrated in FIGS. 1 through 10 are preferably made from bioresorbable material, in particular a polymer poly-β-hydroxybutyric acid (PHB), poly-ε-caprolacton (PCL) and poly-L-lactide (PLLA). A polymer blend of 80% PLLA, 10% PCL and 10% triethylcitrate (TEC) is also highly suitable.

The dimensions of the coronary stents of FIGS. 1 through 10 in the expanded condition are as follows: diameters between 2 and 6 mm and lengths between 6 and 40 mm. On average, those coronary stents involve diameters of 3.5 and 4 mm and lengths of about 20 mm.

Figure 2:
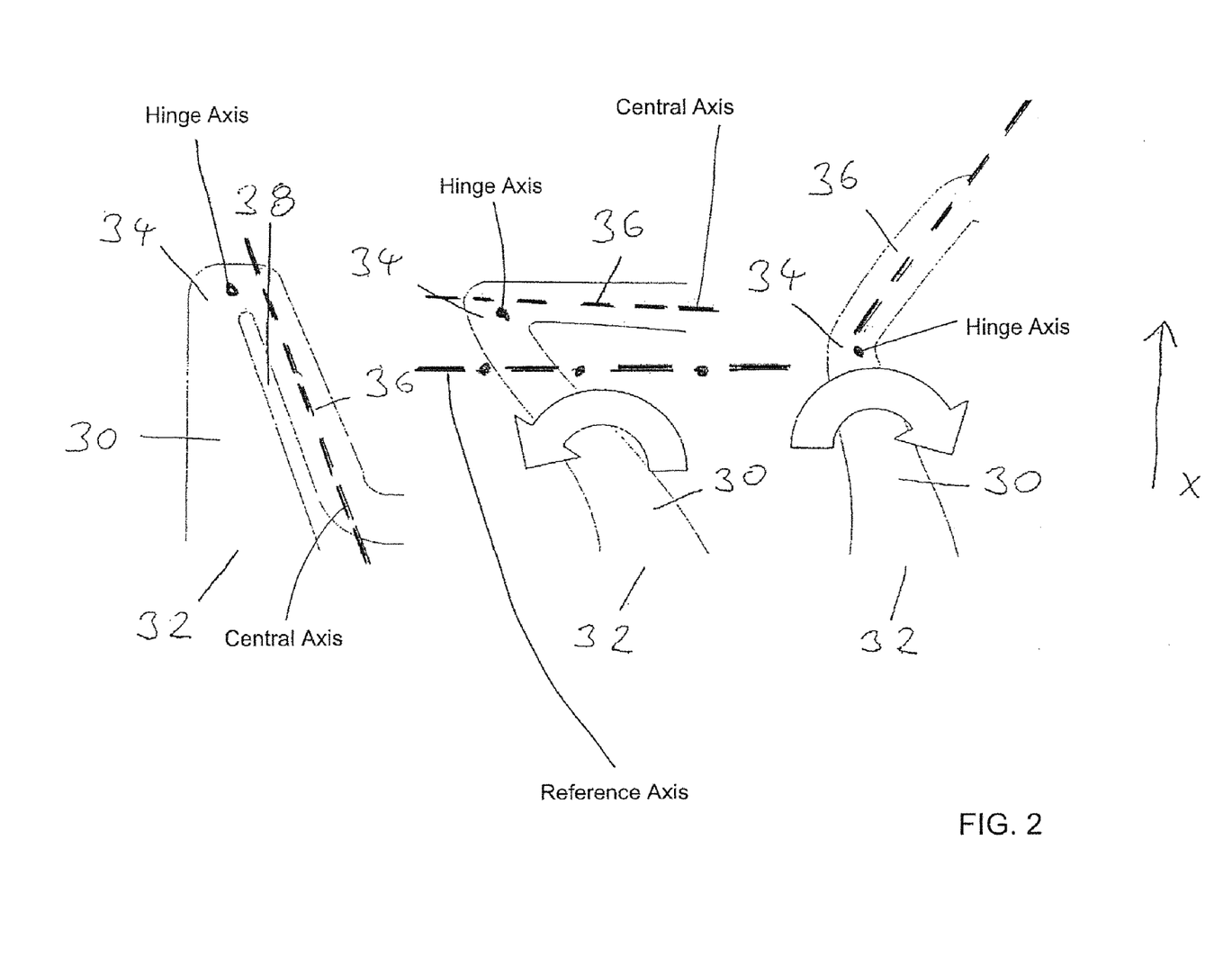

FIG. 2 shows the co-operation of the essential structural elements of a bearing structure in three conditions, namely, at the left in the compressed condition of the bearing structure, in the center in a transitional condition from the compressed to the expanded condition of the bearing structure, and at the right in the expanded condition of the bearing structure. A spring strut 30 extends from an anchor region 32 to an elastically resilient end 34. A hinge strut 36 adjoins the resiliently deflectable end 34 of the spring strut 30. An expansion direction x is shown at the right in FIG. 2. A central axis of the hinge strut is shown as a dashed line extending along the length of hinge strut 36. A hinge axis extends perpendicular to the plane of FIG. 2 at the intersection of spring strut 30 and hinge strut 36, as shown in FIG. 2, as the hinge axis extends transversely with respect to the bearing structure. A reference axis is shown in the center of FIG. 2 as a combined dashed and dotted line. The reference axis extends transversely with respect to the expansion direction and transversely with respect to the hinge axis.

In the compressed condition of the bearing structure as shown on the left, the hinge strut 36 bears closely against the spring strut 30. The spring strut 30 and the hinge strut 36 are separated from each other by a cut 38. The longitudinal axis of a stent corresponding to the view extends in parallel relationship with a horizontal line in the plane of the illustration in FIG. 2. Radial expansion of such a stent corresponds to expansion of the bearing structure in the direction indicated by x in FIG. 2.

The consequence of expansion of the structure in FIG. 2 is that the hinge strut 36 is pivoted in the direction indicated by x. In that way, the spring strut 30 is resiliently deflected in the direction shown by the wide arrow in the middle view in FIG. 2. At the same time, the spring strut 30 applies to the hinge strut 36 a moment which acts in opposite relationship to the direction of the arrow. In the middle view in FIG. 2, a center line of the hinge strut 36 extends approximately in the direction of a reference line which extends in parallel relationship with the longitudinal axis of the stent and at the same time in parallel relationship with a horizontal line in the plane of the view in FIG. 2.

The right view in FIG. 2 corresponds to the expanded condition of a bearing structure. The center line of the hinge strut 36 is pivoted beyond the reference line—that is to say, beyond the condition illustrated in the central view—with the consequence that the spring strut 30 can recoil in the direction shown by the broad arrow in the right view in FIG. 2. Accordingly, in the expanded condition of the bearing structure, the spring action emanating from the spring strut 30 promotes the orientation of the hinge strut 36. In that way, the expanded condition of the bearing structure is stabilized by the spring action emanating from the spring strut 30. That enhances the radial strength of an expanded stent with a bearing structure as described herein.

It can already be seen from FIG. 1a that the spring struts 12 are arranged in pairs and enclose a respective hinge strut between them. That serves for further enhancing radial strength. This arrangement of the struts, which is selected for all variants illustrated in FIGS. 1 through 13, affords the possibility of markedly configuring a kind of pair of spring struts which, after expansion, acts jointly on a hinge strut and thus prevents or reduces the recoil effect.

Due to the expansion action, the left spring strut of a pair of spring struts is urged towards the left and stores energy as a kind of leaf spring.

The right-hand spring strut of the same pair of spring struts is urged towards the right and also stores energy. As soon as the spring struts have slid past each other or the hinge strut is pivoted beyond the reference line, the spring struts return due to the stored energy, as shown in the right view in FIG. 2, and prevent recoil. The spring struts are dimensioned approximately in accordance with the loadings involved, if reference is directed in respect of the loadings involved to the expansion process and not to the radial strength.

The S-shaped hinge struts adopted for the coronary stents in FIGS. 1 through 10 are of a small structural height so that they can be favorably distributed over the small periphery of a coronary stent. In addition, S-shaped hinge struts can be easily connected to pairs of spring struts whose markedness however is not so clearly noticeable as in the case of alternatively possible spiral-shaped struts as are provided for the urethra stents shown in FIGS. 11 through 13. Spiral-shaped struts are of a larger structural height and therefore cannot be distributed in a sufficient number over the relatively small periphery of a coronary stent.

It can already be seen from FIG. 1a that end regions of the cuts 18 are of an enlarged configuration to reduce the edge fiber stretching effect in the transitional region from a resiliently deflectable end of a spring strut 12 to the adjoining hinge strut 16. The corresponding end portions of the cuts 18 are identified by 22 in FIG. 1a.

Figure 3:
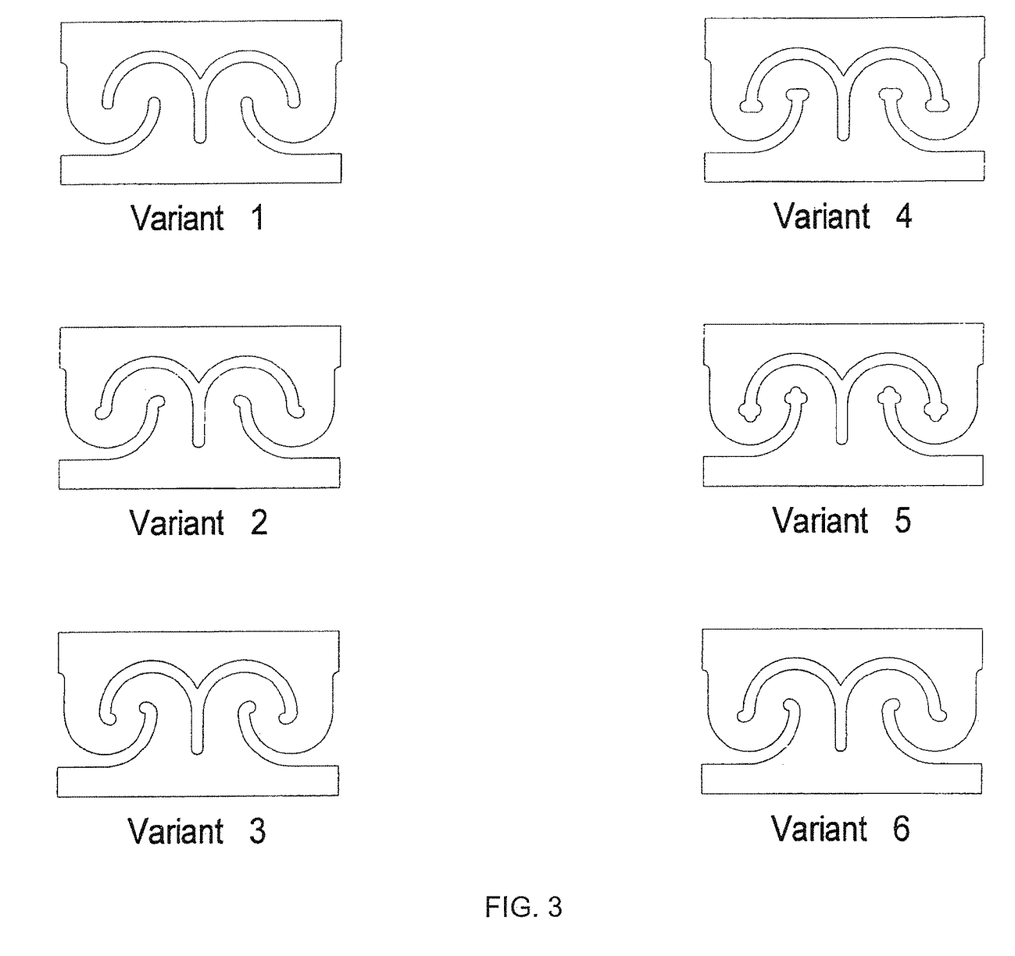
FIG. 3 shows six variants in regard to the configuration of the end region of the cuts for the bearing structure of FIG. 1.

FIG. 3 shows various variants of the configuration for the cuts which separate spring struts and hinge struts from each other. FIG. 3 shows in particular six variants of possible configurations in respect of the bending radii at the end of a respective cut, wherein variant I represents as an initial shape a design with S-shaped struts. Variants 2, 3 and 6 use a kind of termination arc to increase the bending radius, while a straight termination line is added to variants 4 and 5. The configurations of the end regions of the cuts, which are shown in variants 2 through 6, provide that edge fiber stretching upon expansion of the bearing structure in the transitional region from a spring strut to a hinge strut is advantageously reduced.

The variants 3, 4 and 5 afford the least edge fiber stretching. If the recoil is to be kept as slight as possible, the variants 3 and 5 are to be preferred to the others.

The variant 5 in FIG. 3 corresponds in that respect to the embodiment of FIGS. 1a and 1b. Besides the end of the cut being rounded off, the variant 1 shown in FIG. 3 does not involve any particular features for reducing edge fiber stretching. The variants 3, 4, 5 and 6 in regard to the configuration of the end region of cuts, like the cuts 18 in FIG. 1, each afford a respective transitional region between the elastically deflectable end of a spring strut and the adjoining hinge strut which is reduced in its cross-section with respect to the cross-section of the spring strut and the hinge strut. A transitional region of that kind, of reduced cross-section, has a pivot joint-like action.

Figure 4A:
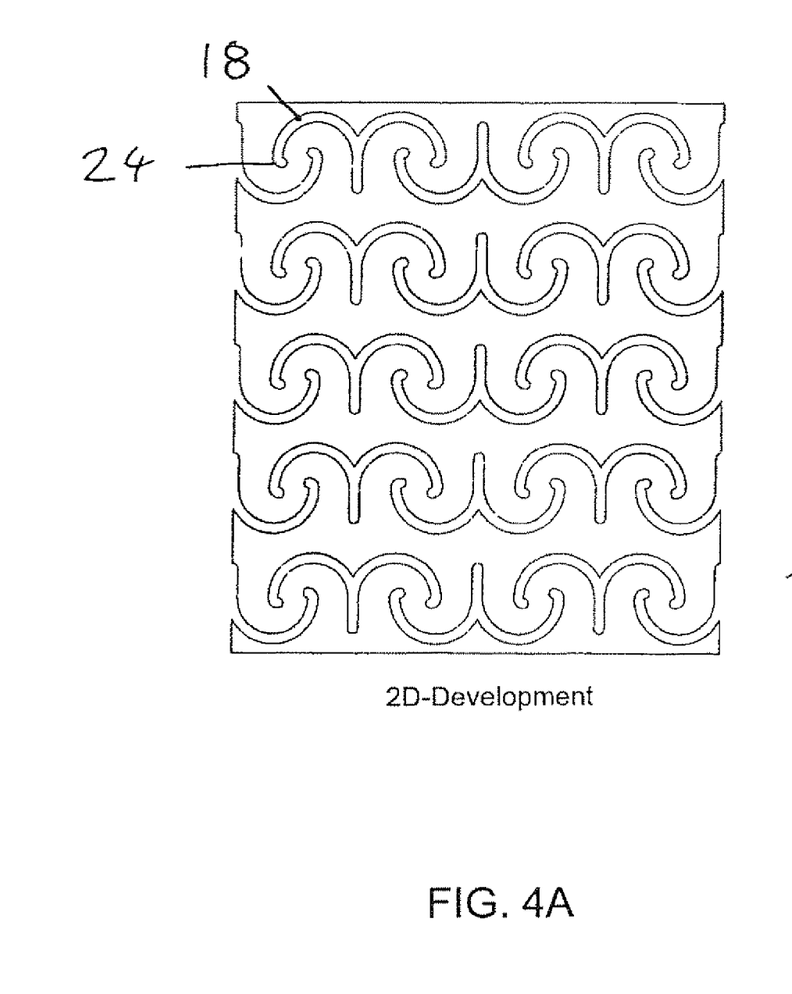
FIG. 4a shows a development of a bearing structure for a second variant of a coronary stent.
Figure 4B:
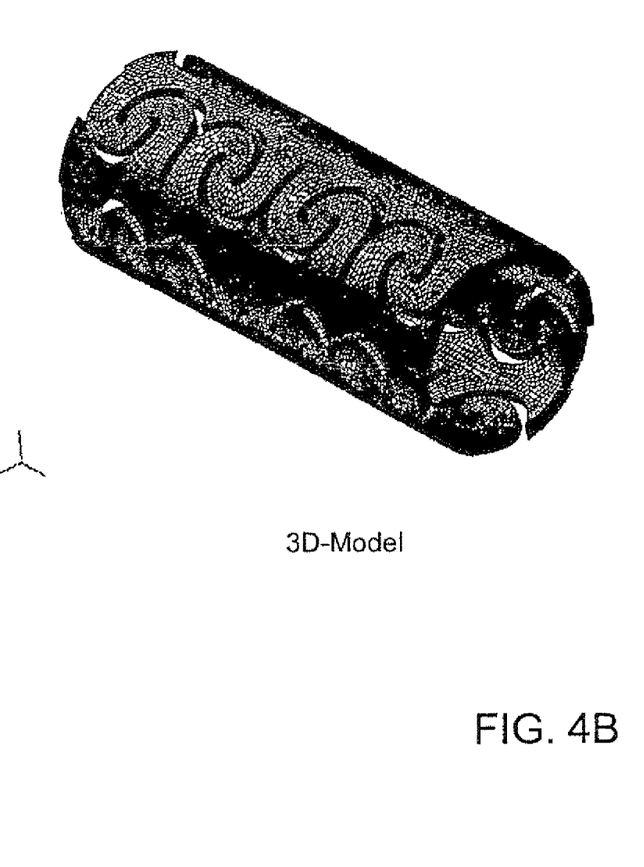
FIG. 4b shows a 3D-model of a portion of the second variant of a stent corresponding to the development of FIG. 4a, FIG. 5a shows a development of a bearing structure for a third variant of a coronary stent.

The second variant of a coronary stent, as is shown in FIGS. 4a and 4b, differs the variant illustrated in FIGS. 1a and 1b only in respect of the configuration of the end regions 24 of the cuts 18. The configuration of the end portions 24 of the cuts 18 corresponds to the variant 3 in FIG. 3.

Figure 5A:
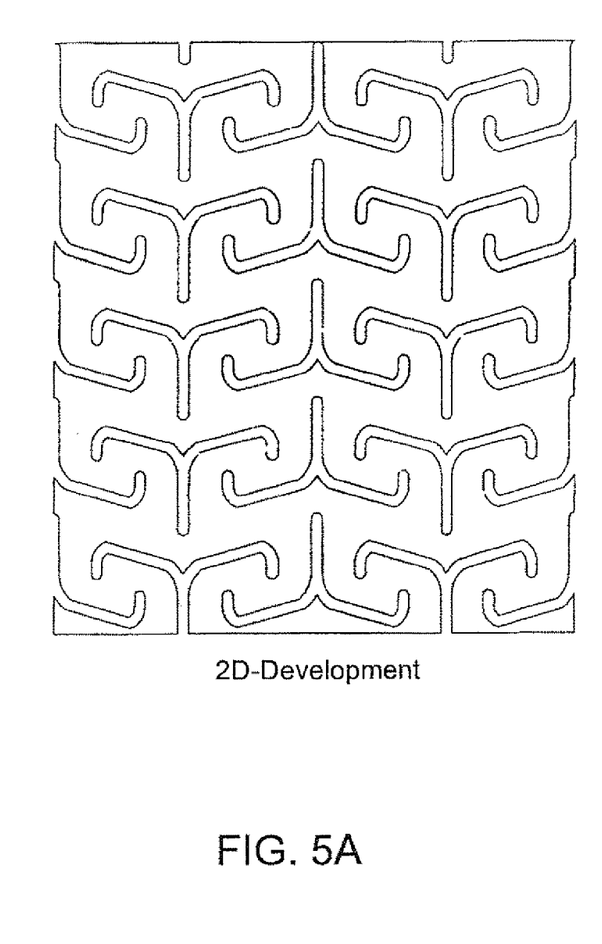
Figure 5B:
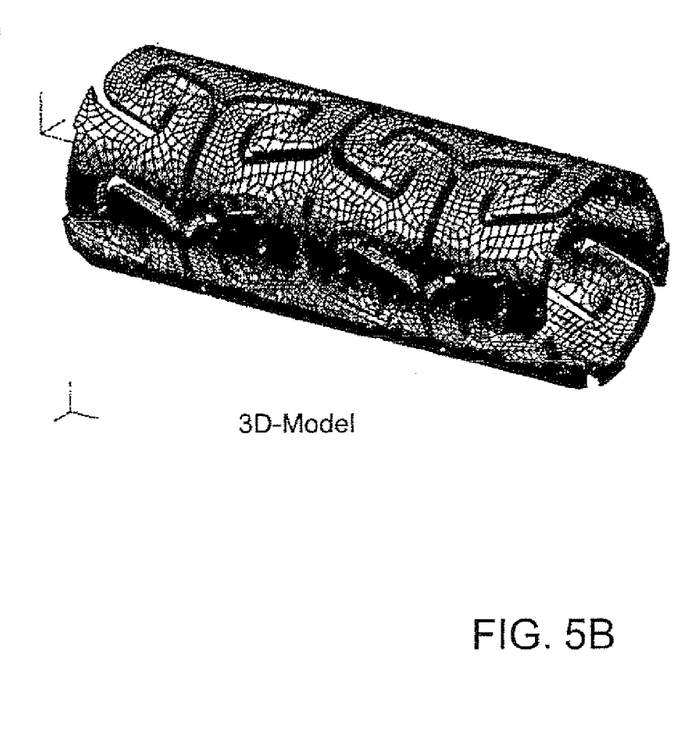
FIG. 5b shows a 3D-model of a stent portion in accordance with the third variant with the development of FIG. 5a, FIG. 6a shows a development of a bearing structure for a fourth variant of a coronary stent.

The third embodiment of a coronary stent, as is illustrated in FIGS. 5a and 5b, embodies a design which combines S-shaped struts with angular struts. The combined design provides that the stent increases in length during expansion until the longitudinal struts "flip over". After flipping-through of the zig-zag line, the stent is reduced in length again. A spring-back effect is made more difficult in that way so that the recoil is less.

Figure 6A:
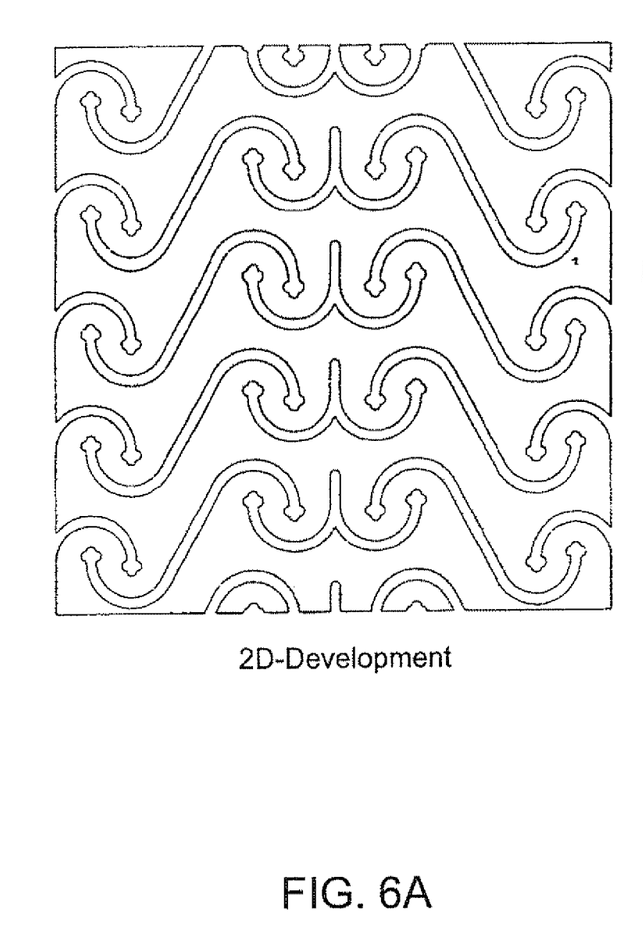
Figure 6B:
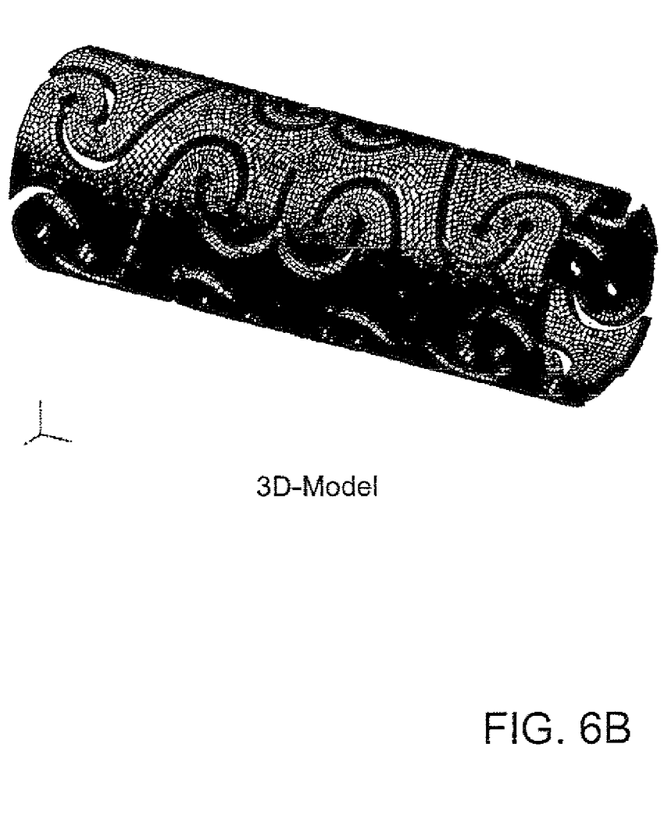
FIG. 6b shows a 3D-model of a portion of the fourth variant of a stent corresponding to the development of FIG. 6a, FIG. 7a shows a development of a bearing structure for a fifth variant of the coronary stent.
Figure 7A:
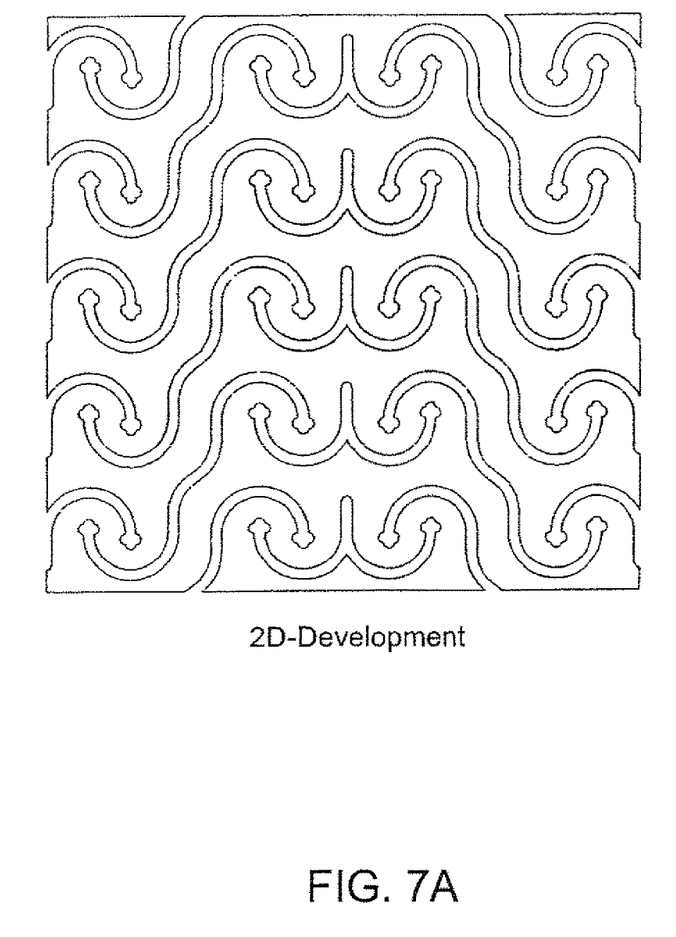
Figure 7B:
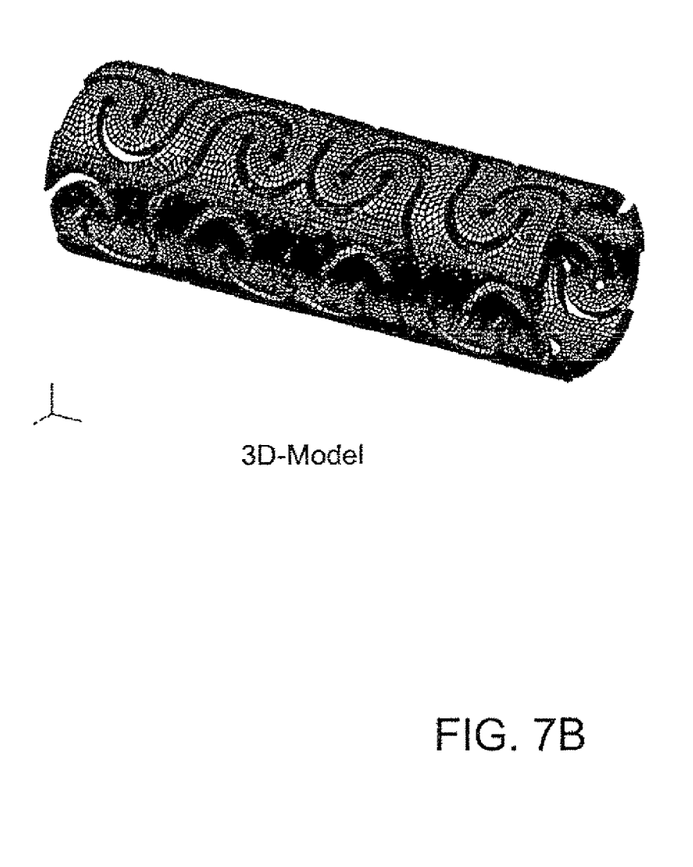
FIG. 7b shows a 3D-model of a portion of the fifth variant of the coronary stent corresponding to the development from FIG. 7a, FIG. 8 shows a side view of a stent portion corresponding to the fifth variant in FIGS. 7a and b.
Figure 8:
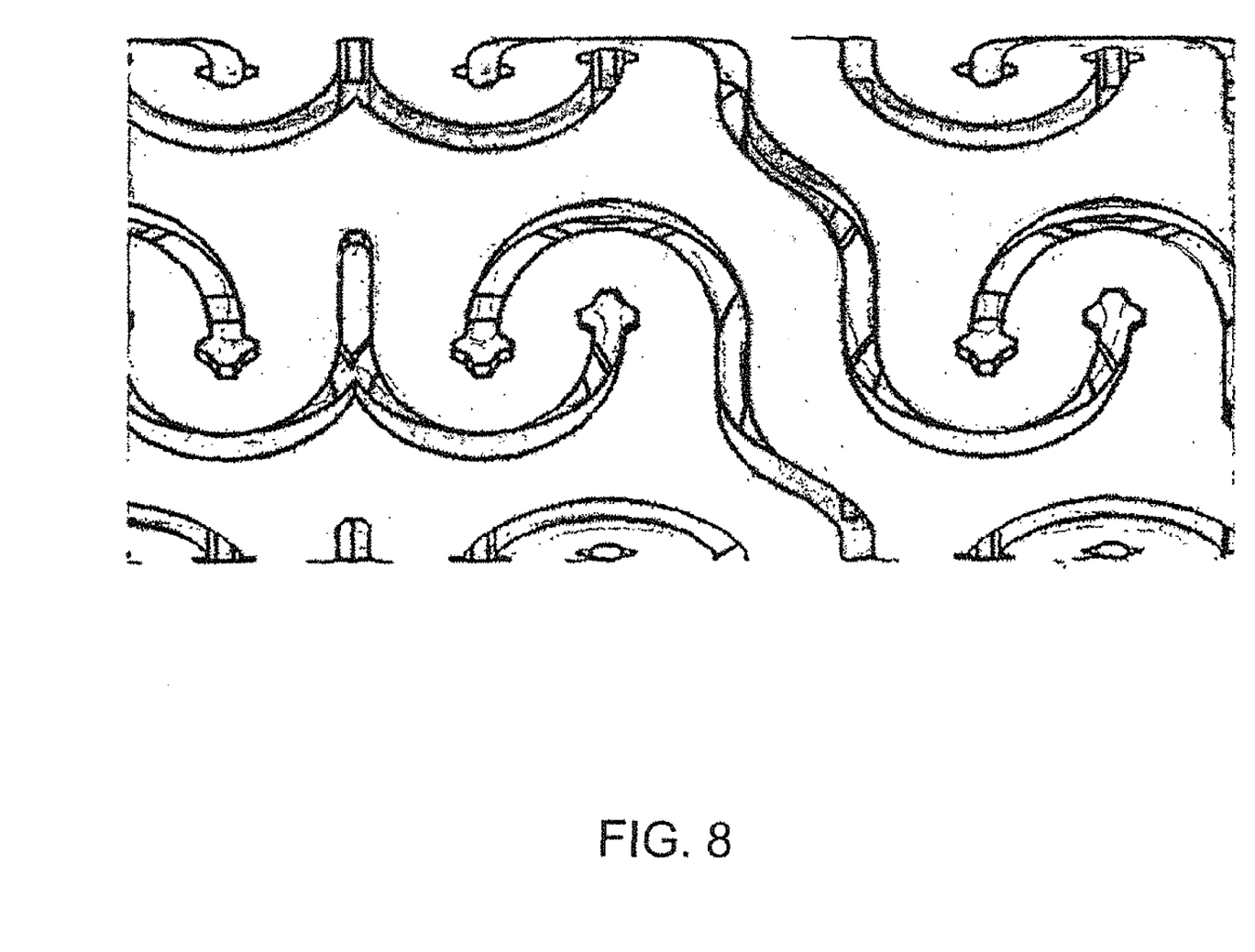
Figure 9:
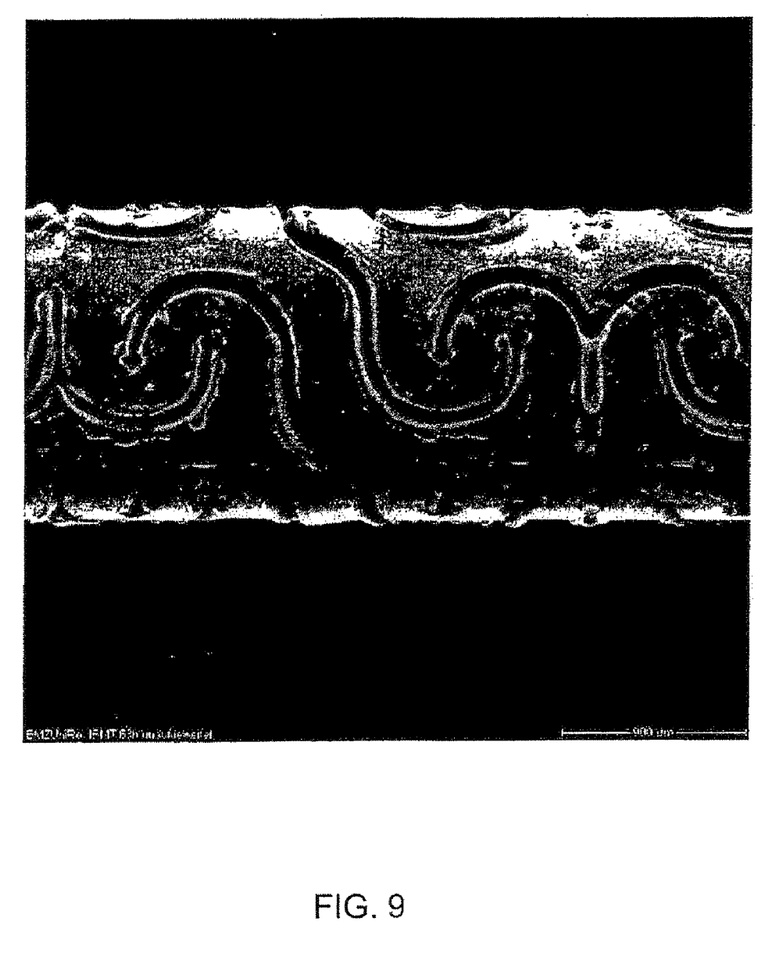
FIG. 9 shows a photograph of the variant of FIGS. 7a through 8, showing the compressed condition of the fifth variant.
Figure 10:
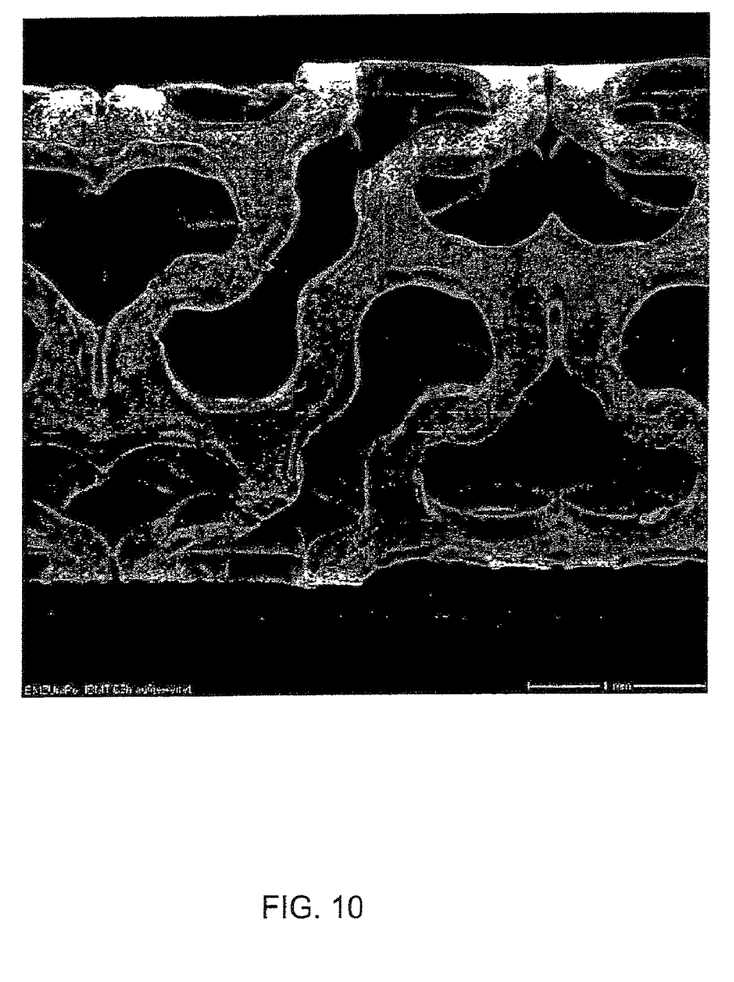
FIG. 10 shows a photograph of the fifth variant of FIG. 9 in the expanded condition.

FIGS. 6 and 7 show designs for coronary stents with enhanced radial strength. Mutual displacement of adjacent rings formed by pairs of spring struts which occur in succession in the radial direction, with hinge struts disposed therebetween, serves to increase the level of radial strength. That affords a zig-zag line in respect of stiffness. In the ideal situation, after expansion soft regions lie beside stiff regions on a line along the axis of the stent, whereby the struts only fail due to buckling under relatively high pressures.

In the design shown in FIG. 6, the displacement between the struts is half an element height while in FIG. 7 it is a full element height. The term element height is used here to denote the radial extent of a pair of spring struts with hinge strut disposed therebetween.

Figure 11A:
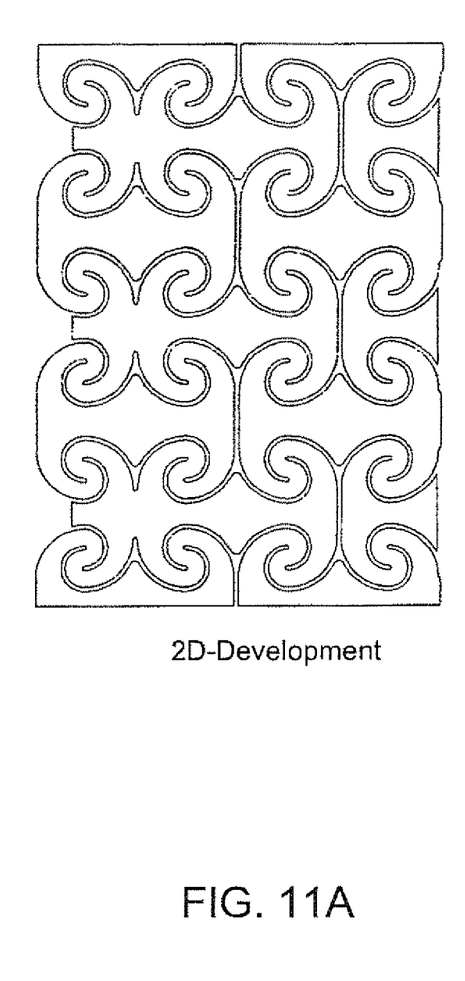
FIG. 11a shows the development of a bearing structure for a first variant of urethra stent.
Figure 11B:
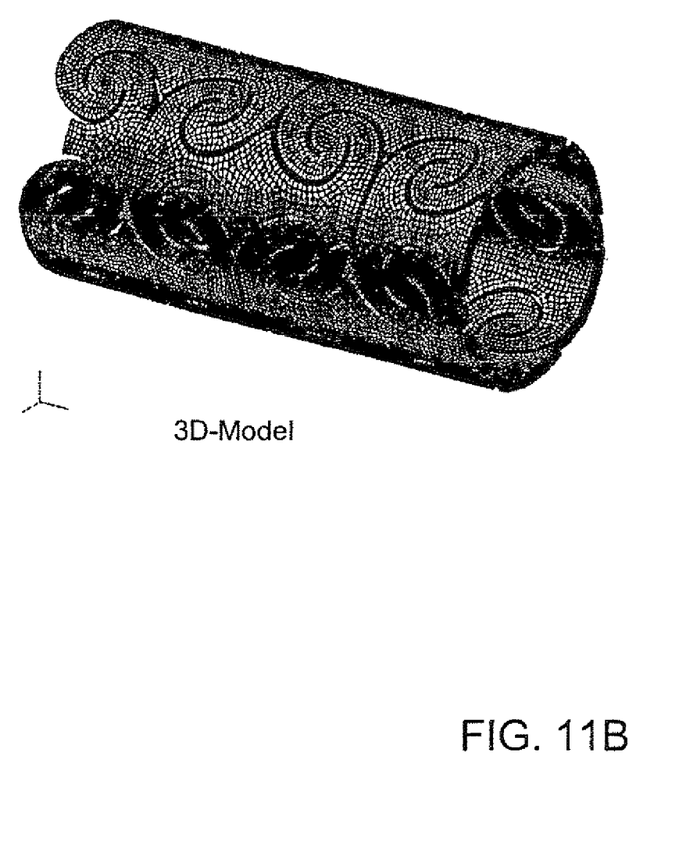
Figure 12A:
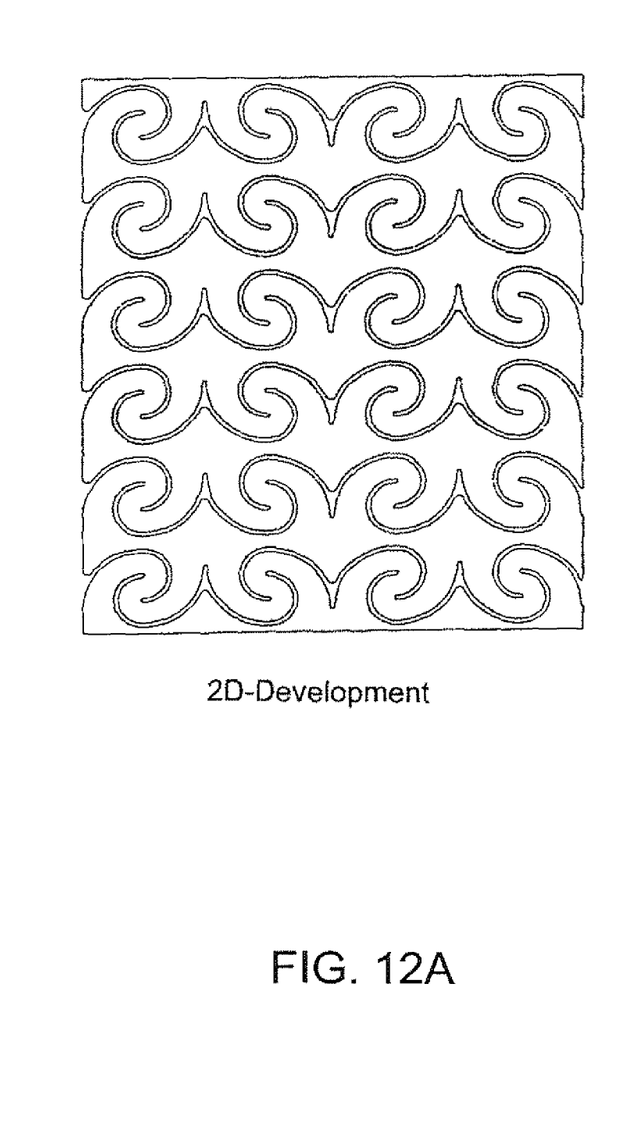
Figure 12B:
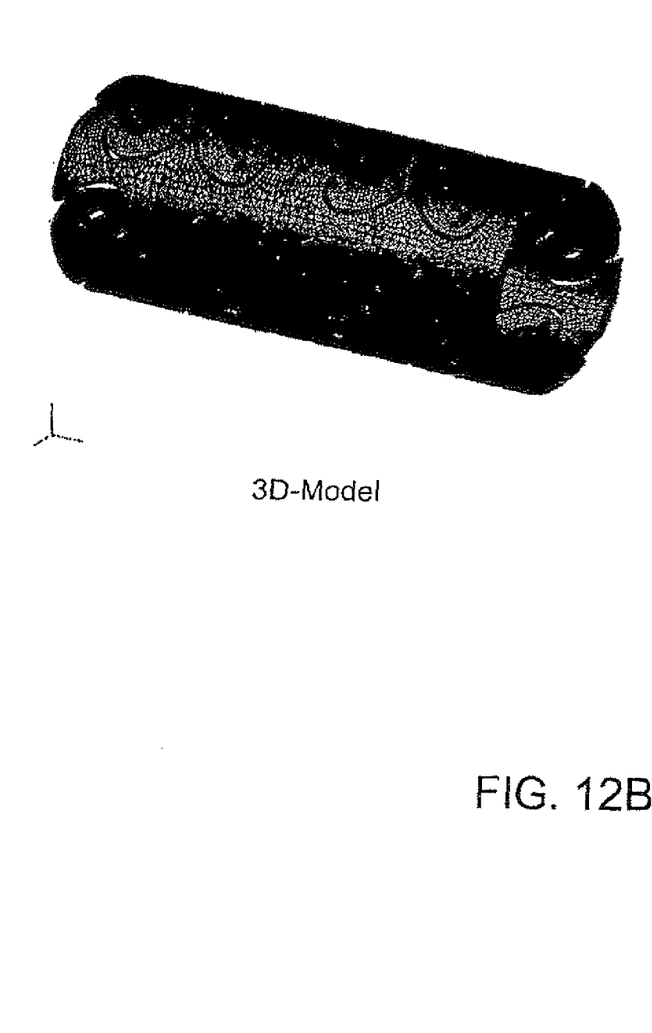
FIG. 12b shows a 3D-model of the second variant for a urethra stent with a development as shown in FIG. 12a, FIG. 13a shows a 3D-model of the second variant of FIGS. 12a and 12b showing both the compressed condition of that variant and also the balloon-expanded condition of the variant.
Figure 13A:
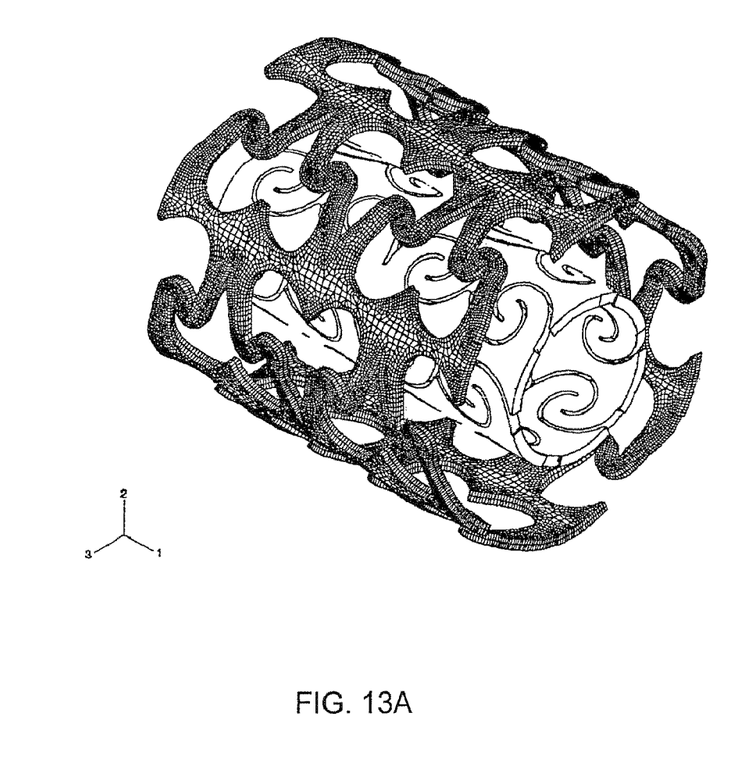
Figure 13B:
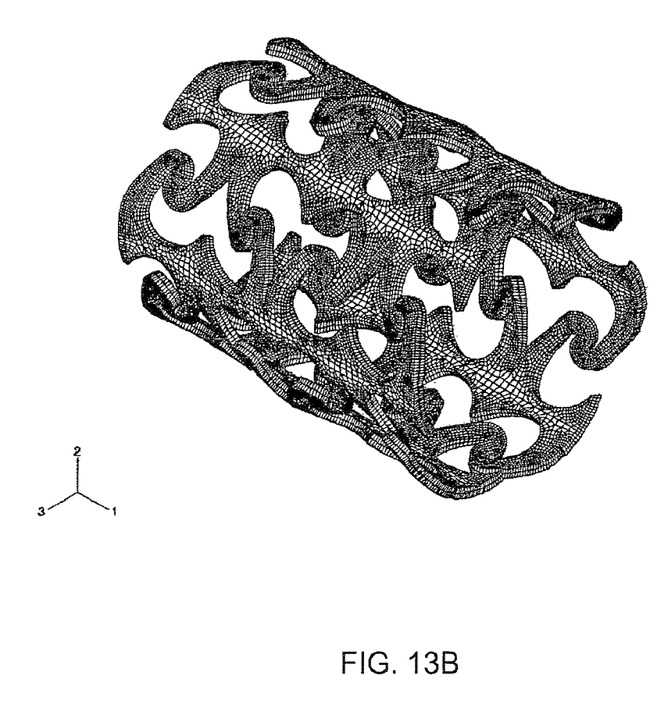
FIG. 13b shows the second variant of the urethra stent after elastic recoil.

FIGS. 11 through 13 show urethra stents. They are of a larger diameter of about 10 mm, in comparison with coronary stents. That makes it possible for the illustrated spiral design to be imparted to the hinge struts.

The flexural stiffness of the stent designs set forth here is based on the continuous limbs which extend over the entire stent length. It can be reduced by continuous limbs in the longitudinal direction of the stent being severed.

We claim:

1. A one-piece expandable flat bearing structure comprising at least partially elastically deformable struts which are separated from each other by openings in the bearing structure, the struts including:

spring struts having an anchor region on a first end and extending to a resiliently deflectable second end, the spring struts being elastically resilient with respect to the anchor regions, hinge struts adjoining said spring struts at the resiliently deflectable second ends of the spring struts, forming a hinge axis at the juncture of a spring strut and a hinge strut, the hinge axis extending transversely with respect to the bearing structure at the juncture of the spring strut and the hinge strut, and each hinge strut having a central axis, wherein the bearing structure can assume at least one compressed condition, at least one transitional condition, and at least one expanded condition and wherein the bearing structure has at least one expansion direction, and wherein a reference axis extends within the bearing structure in approximately parallel relationship with a longitudinal axis of the bearing structure and transversely with respect to the expansion direction and transversely with respect to the hinge axis, wherein the spring struts and the hinge struts are of such a configuration and arrangement that the bearing structure is capable of going from a compressed condition to a transitional condition, to an expanded condition, and wherein in the compressed state, the spring strut and hinge strut bear closely against each other and are separated by cuts, and the central axis of the hinge strut is transverse to the reference axis, and wherein in the transitional condition, the hinge strut is pivoted at the hinge axis in an expansion direction of the bearing structure such that the central axis of the hinge strut is approximately parallel to the reference axis and the spring struts rotate in a first direction such that the spring struts are initially resiliently deflected transversely to the expansion direction of the bearing structure, and wherein in the expanded condition, the hinge strut additionally pivots at the hinge axis in the expansion direction of the bearing structure beyond the reference axis such that the central axis of the hinge strut is transverse to the reference axis and the spring struts rotate in a second direction opposite to the first direction, thereby providing that both the compressed condition of the bearing structure and also the expanded condition of the bearing structure are stabilized by a spring action emanating from the spring struts.

2. A bearing structure as set forth in claim 1, wherein a respective spring strut adjoins both longitudinal ends of a respective hinge strut and said two spring struts are so arranged relative to each other that they exert a moment in the same direction on the hinge strut about the hinge axis.

3. A bearing structure as set forth in claim 2, wherein the two spring struts respectively adjoining a hinge strut are shaped and arranged in point-symmetrical relationship with each other.

4. A bearing structure as set forth in claim 1, wherein the bearing structure forms a peripheral wall of a stent.

5. A bearing structure as set forth in claim 4, wherein the expansion direction extends in the peripheral direction of the stent while the hinge axis is oriented approximately radially.

6. A bearing structure as set forth in claim 1, comprising plastic material.

7. A bearing structure as set forth in claim 1, comprising a magnesium alloy.

8. A bearing structure as set forth in claim 1, comprising a bioresorbable material.

9. A bearing structure as set forth in claim 1, wherein the cuts are of such a configuration as to provide hinge struts which are S-shaped or W-shaped in the compressed condition.

10. A bearing structure as set forth in claim 9, wherein the cuts are expanded in end regions of the cuts to reduce a notch effect.

11. A bearing structure as set forth in claim 1, wherein in the proximity of the anchor regions, the spring struts are of a larger cross-sectional area than in the region of their resiliently deflectable ends.

12. A bearing structure as set forth in claim 11, wherein the spring struts steadily taper from the anchor regions towards the resiliently deflectable ends.

13. A bearing structure as set forth in claim 1, wherein the hinge struts are of a substantially uniform cross-section transversely with respect to their central axis.

14. A bearing structure as set forth in claim 1, wherein a transitional region of a cross-section which is reduced in relation to the hinge strut is provided between a respective resiliently deflectable end of a spring strut and the hinge strut adjoining the resiliently deflectable end.

15. A bearing structure as set forth in claim 1, wherein the cuts are expanded in end regions of the cuts to reduce a notch effect.

* * * * *